United States Patent
Burg et al.

(10) Patent No.: US 9,849,452 B2
(45) Date of Patent: Dec. 26, 2017

(54) MATERIALS TRANSPORT DEVICE FOR DIAGNOSTIC AND TISSUE ENGINEERING APPLICATIONS

(71) Applicant: Clemson University, Clemson, SC (US)

(72) Inventors: Karen J. L. Burg, Manhattan, KS (US); Suzanne Tabbaa, Westlake, OH (US)

(73) Assignee: University of Georgia, Athens, GA (US)

( * ) Notice: Subject to any disclaimer, the term of this patent is extended or adjusted under 35 U.S.C. 154(b) by 14 days.

(21) Appl. No.: 14/541,823

(22) Filed: Nov. 14, 2014

(65) Prior Publication Data

US 2015/0241320 A1    Aug. 27, 2015

Related U.S. Application Data

(60) Provisional application No. 61/904,167, filed on Nov. 14, 2013.

(51) Int. Cl.
| | | |
|---|---|---|
| *B01L 3/00* | (2006.01) | |
| *G01N 1/14* | (2006.01) | |
| *G01N 30/52* | (2006.01) | |

(52) U.S. Cl.
CPC ............ *B01L 3/502* (2013.01); *B01L 3/5025* (2013.01); *B01L 3/5023* (2013.01);
(Continued)

(58) Field of Classification Search
CPC ................... B01L 2300/041; B01L 2300/0838
(Continued)

(56) References Cited

U.S. PATENT DOCUMENTS

| 4,187,333 A | 2/1980 | Rembaum et al. |
| 4,286,005 A | 8/1981 | Berger |
| (Continued) | | |

FOREIGN PATENT DOCUMENTS

WO    WO91/12949    9/1991

OTHER PUBLICATIONS

Nelson et al., "A Novel Stationary Phase: Capillary-Channeled Polymer (C-CP) Fibers for HPLC Separations of Proteins," *Journal of Chromatographic Science*, vol. 41, Oct. 2003, pp. 475-479.
(Continued)

*Primary Examiner* — Natalia Levkovich
(74) *Attorney, Agent, or Firm* — Dority & Manning, PA

(57) ABSTRACT

Devices that can transport biological materials are described. The devices incorporate capillary channeled fibers that can effectively transport living cells as well as other biological materials such as nutrients, growth factors, waste materials, etc. The devices can include a sorptive material at one end of the fibers that can improve transport of materials through the devices. The devices can differentially transport different cell types, particularly when the fibers are held in a vertical orientation. Diagnostic devices that incorporate the capillary channeled fibers are described that can be utilized to separate cell types from one another. Tissue engineering scaffolds that incorporate the capillary channeled fibers are described that can more efficiently transport materials into and out of the scaffolds.

19 Claims, 9 Drawing Sheets

(52) U.S. Cl.
CPC ... *B01L 2200/025* (2013.01); *B01L 2200/026* (2013.01); *B01L 2200/0631* (2013.01); *B01L 2200/0647* (2013.01); *B01L 2300/041* (2013.01); *B01L 2300/042* (2013.01); *B01L 2300/069* (2013.01); *B01L 2300/0609* (2013.01); *B01L 2300/0829* (2013.01); *B01L 2300/0838* (2013.01); *B01L 2300/161* (2013.01); *B01L 2400/0406* (2013.01); *C12N 2535/00* (2013.01); *G01N 2001/149* (2013.01); *G01N 2030/521* (2013.01)

(58) Field of Classification Search
USPC .................................................. 422/507, 535
See application file for complete search history.

(56) References Cited

U.S. PATENT DOCUMENTS

| | | | |
|---|---|---|---|
| 4,391,716 A | 7/1983 | McCurry | |
| 4,657,742 A | 4/1987 | Beaver | |
| 4,758,341 A * | 7/1988 | Banner | B01D 53/22 210/232 |
| 5,158,680 A * | 10/1992 | Kawai | B01D 63/022 210/321.61 |
| 5,234,594 A | 8/1993 | Tonucci et al. | |
| 5,800,897 A | 9/1998 | Sharma et al. | |
| 5,855,798 A | 1/1999 | Phillips et al. | |
| 5,876,918 A | 3/1999 | Wainwright et al. | |
| 5,972,505 A | 10/1999 | Phillips et al. | |
| 6,127,036 A | 10/2000 | Xue et al. | |
| 6,270,674 B1 | 8/2001 | Baurmeister et al. | |
| 6,656,360 B2 | 12/2003 | Rohrbach et al. | |
| 6,991,652 B2 | 1/2006 | Burg | |
| 7,261,813 B2 | 8/2007 | Marcus et al. | |
| 7,374,673 B2 | 5/2008 | Marcus | |
| 7,740,763 B2 | 6/2010 | Marcus et al. | |
| 8,293,531 B1 | 10/2012 | Burg et al. | |
| 8,475,531 B1 | 7/2013 | Maxson et al. | |
| 2005/0023221 A1 | 2/2005 | Marcus | |
| 2007/0071649 A1 | 3/2007 | Marcus | |
| 2008/0213823 A1 | 9/2008 | Christensen et al. | |

OTHER PUBLICATIONS

Marcus et al., "Capillary-channeled polymer fibers as stationary phases in liquid chromatography separations," *Journal of Chromatography A*, vol. 986, 2003, pp. 17-31.

* cited by examiner

MATERIALS TRANSPORT DEVICE FOR DIAGNOSTIC AND TISSUE ENGINEERING APPLICATIONS

CROSS REFERENCE TO RELATED APPLICATION

This application claims filing benefit of U.S. Provisional Patent Application Ser. No. 61/904,167 having a filing date of Nov. 14, 2013, which is incorporated herein in its entirety by reference.

FEDERALLY SPONSORED RESEARCH AND DEVELOPMENT

This invention was made with government support under contract number W81XWH-05-1-0379 and NSF Grant No. 0736007, awarded by the U.S. Department of Defense. The government has certain rights in the invention.

BACKGROUND

Efficient methods to identify and evaluate particular cell types would be useful in a wide variety of applications. For instance, cellular diagnostic testing, e.g., the diagnosis of disease states based upon the presence or absence of certain cell types, ideally utilizes testing protocols that can provide both speed and accuracy, as well as ease of use. By way of example, cancer, which is the world's deadliest and most costly disease requires the accurate recognition of the presence of cancer cells for proper diagnosis. Moreover, as early diagnosis can be key in improved survival rates, testing protocols that can recognize cancer cells at very low concentration are of great benefit.

While current cancer testing protocols such as histology/cytology testing, immunoassays, flow cytometry, and so forth have improved cancer screening and cancer survival rates, room for improvement in the art exists. For example, many testing protocols require multiple expensive tests to make a confident diagnosis, and protocols often lack high reliability. Testing methods are often complicated and require complex procedures that can increase prices. In addition, testing often is inadequate to distinguish the state of a cancer, for instance failing in distinguishing benign cancer cells from malignant cancer cells. Thus, a reliable and inexpensive device and method that could identify diseased cells in a test sample would be of great benefit.

The ability to quickly and reliably identify particular cell types and/or subpopulations of particular cell types would be of benefit in other applications as well. For instance, a major limitation in developing tissue engineered constructs is the ability to identify and isolate functional cells, typically progenitor cells, from the patient or donor. The ability to reliably and accurately test the function and the cellular make-up of transplant tissue would also be of great benefit to, e.g., prevent the transplant of diseased tissue. Conventional methods to identify and isolate desirable functional cells involve using cell surface markers and morphological traits as well as cell plating and cell adherence methods. However, many cell types lack common markers or universal morphological traits, making reliable testing extremely difficult. Conventional methods are expensive and do not directly evaluate cell function.

The development of engineered tissue constructs faces other difficulties, in addition to identification and utilization of desired progenitor cells. For example, there are currently constraints on the size of tissue constructs that can be created, and a major shortcoming of tissue engineering is that the size of the grafts that can be generated is small relative to the size of the defects that they are meant to treat. For example, autologous osteochondral grafting or mosaicplasty, often referred to as the gold standard for the treatment of cartilage defects and osteoarthritis, fails in the therapy of large lesions measuring more than about 20 millimeters in diameter, and the viable constructs formed to date are considerably smaller than this size.

The size constraints that tissue engineering currently faces are largely due to the non-homogeneous growth of cells on the traditional 'porous block' scaffolds, which prevents the formation of a functional construct from surface to core. This is due to two major limiting factors: lack of uniform cell seeding though the entire thickness of the scaffold and the mass transfer limitations of nutrients and waste removal. Because of the complex architecture of many 3D scaffolds, dispersing a high density of cells with high efficiency and uniformity throughout the scaffold volume is difficult. An additional factor in the survival of thick 3D engineered tissues is the delivery of oxygen and nutrients to the entire construct, and waste removal from the construct. The movement of nutrients to the cells and removal of waste products from the cells has to rely on molecular diffusion due to the lack of a vascular system. As such, nutrients are depleted before reaching the inner core of the construct and waste products accumulate. Cells that migrate into the core become necrotic and the living cell population is commonly concentrated at the periphery of the scaffold. There is also a delay in tissue formation or lack of tissue formation in the center of the scaffold due to the lack of biomolecule/growth factor penetration. An example commonly occurs in posterolateral fusions there is a "lag effect" of bone formation in the center of the scaffold.

What are needed in the art are devices and methods that can transport biological materials effectively. For instance, a device that can transport different cell types at different rates would be beneficial to provide a low cost, fast, and accurate cell recognition protocol. Additionally, a device that can transport biological materials such as cells, nutrients, biomolecules, and waste in a fast and efficient manner would be of benefit in tissue engineering.

SUMMARY

According to one embodiment, disclosed is a device for transporting biological materials. The device includes a plurality of capillary channeled fibers that are adjacent to one another and generally aligned with one another in a bundle. Each of the capillary channeled fibers includes a plurality of co-linear channels extending along the length of the fiber, each channel being defined by a pair of opposed walls that extend longitudinally along the length of the fiber with the opposed walls forming a part of the exterior surface of the fiber. The fibers are held adjacent to one another such that at least one channel is formed between two adjacent capillary channeled fibers of the bundle.

The device also includes a cap that covers one end of the bundle. More specifically, a first end of the bundle of capillary channeled fibers is enclosed within the cap and the cap can include a sorptive material that surrounds the first end of the bundle.

According to another embodiment, disclosed is a diagnostic device. The diagnostic device includes a well that is capable of holding a fluid sample. The diagnostic device also includes a capillary channeled fiber and a brace that secures the capillary channeled fiber in a vertical orientation with a first end of the fiber within the well. For instance, in one embodiment, the brace can be a lid that sits over the well. The lid can include an aperture that passes from a first side to a second side of the lid, and the fiber can be held securely by the lid in a vertical orientation with one end of the fiber within the well.

In one embodiment, the fiber of the diagnostic device can be a member of a bundle of fibers that include capillary channeled fibers. The fibers can be held adjacent to one another and generally aligned with one another such that at least one channel is formed between two adjacent capillary channeled fibers of the bundle. In yet another embodiment, the fiber bundle of the diagnostic device can include a cap that covers one end of the bundle. More specifically, a first end of the bundle can be held within the well and a second end of the bundle can be enclosed within the cap and the cap can include a sorptive material that surrounds the first end of the bundle.

According to another embodiment, disclosed is a tissue engineering scaffold. The tissue engineering scaffold includes a porous matrix of a biocompatible material that can support cell growth and development and also includes a device for transporting biological materials. The device for transporting biological materials includes the bundle of capillary channeled fibers and a cap on one end of the bundle; the cap including a sorptive material that surrounds the end of the bundle of fibers. At least a portion of the bundle of capillary channeled fibers can be enclosed within the porous matrix. The cap that covers one end of the bundle of fibers can be within the porous matrix in one embodiment, and can be external to the porous matrix in another embodiment.

Also disclosed are methods for separating biological materials such as cells or DNA from other materials by use of the devices. For instance, a method can include locating a first end of a materials transport device as disclosed herein within a solution that includes a first cell and a second cell, holding the first end of the fiber (which correlates with the first end of the device) within the solution for a period of time, the first cell wicking through the channels of the fiber to a first location of the materials transport device during the period of time and the second cell wicking through the channels of the fiber to a second location of the materials transport device during the period of time. The method can also include recovering at least one of the first cell or the second cell from the materials transport device.

BRIEF DESCRIPTION OF THE FIGURES

The presently disclosed subject matter may be better understood with reference to the Figures, of which:

FIG. 2 illustrates the cell separation capabilities of a materials transport device as disclosed herein.

DETAILED DESCRIPTION

Figure 1:
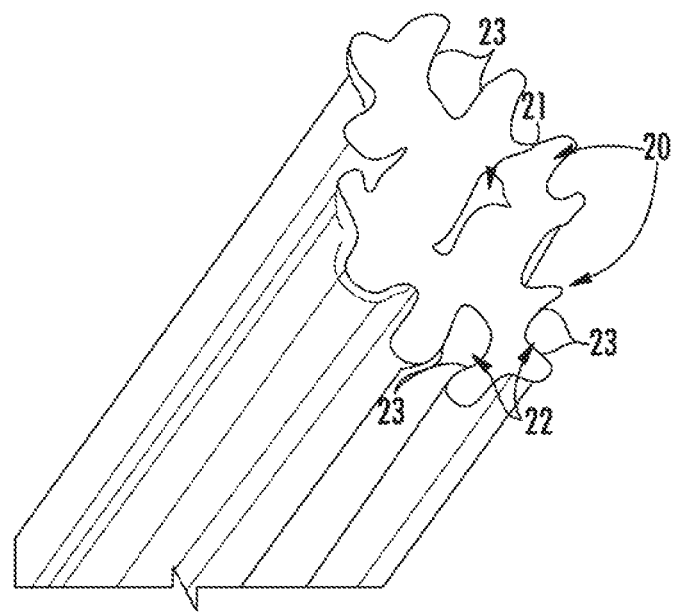
FIG. 1 illustrates a bundle of two capillary channeled fibers as may be incorporated in a materials transport device as disclosed herein.

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made to the disclosed subject matter without departing from the scope or spirit of the disclosure. For instance, features illustrated or described as part of one embodiment may be used with another embodiment to yield a still further embodiment.

In general, the present disclosure is directed to devices that can transport biological material. More specifically, disclosed devices incorporate capillary channeled fibers that can effectively transport living cells as well as other biological materials such as nutrients, growth factors, waste materials, etc.

Beneficially, it has been discovered that capillary channeled fibers can differentially transport different cell types, particularly when the fibers are held in a vertical orientation. This has led to the development of diagnostic devices that can be utilized to separate cell types from one another. For instance, the diagnostic devices can isolate cancer cells from healthy cells in a heterogeneous cellular solution. Moreover, in addition to separating cells of different types, cells that can be separated from one another by use of the diagnostic devices can include similar cell types at a different stage of disease or development as well as polynucleic acids (DNA and RNA) from other materials. For instance, cancerous cells can be separated from healthy cells of the same type (e.g., cancerous breast cancer cells can be separated from healthy breast epithelial cells) as well as from other cancer cells of the same type that have varying metastatic capabilities, and progenitor cells can be separated from further differentiated cells (e.g., mesenchymal stem cells can be separated from macrophage cells).

According to one embodiment, the capillary channeled fibers can be combined with a sorptive material that can function as a pump to encourage flow of biological materials through the fibers and provide temporal/spatial transport of cells or other biomolecules. While this element can be of great benefit in the diagnostic devices, it has also provided a route to formation of tissue engineering scaffolds that can more effectively transport biological materials into and out of the scaffolds and the associated developing cellular construct. Without wishing to be bound to any particular theory, it is believed that the improved capillary action provided by the sorptive material of the device can improve transport of materials (e.g., cells, growth factors, etc.) into the interior of the scaffold and can also provide for the movement of materials to and from the cells following location of the cells in the interior of the scaffold. The construct can also improve the initial cell seeding and infiltration of a scaffold by distribution cells homogeneously. The improved transport properties throughout the scaffold can provide for viable cells throughout a cellular construct. Moreover, the improved viability of the cells within the construct can be maintained without the necessity of perfusion under pressure of the culture media. Accordingly, the cellular construct can better maintain viability, for instance following removal from an in vitro environment to an in vivo environment, i.e., following implant.

Capillary channeled fibers as may be utilized in the devices can include any fiber that incorporates one or more open channels along the axial length of the fiber. Thus, the capillary channeled fibers may also be referred to as lobed fibers, channeled fibers of non-circular cross section, or the like. For example, and with reference to FIG. 1, channeled fibers 20 define a non-circular cross section and include a plurality of co-linear channels 22 extending along the axial length of the exterior surface of the fiber 20. Each channel 22 is defined by a pair of opposed walls 23 that extend longitudinally along a length of the fiber and form part of the exterior surface of the fiber 20. In one embodiment, these channels 22 and walls 23 extend down the entire length of the fiber 20 parallel to the longitudinal axis of the fiber 20 and are co-linear on each fiber 20. Examples of suitable capillary-channeled fibers have been described in U.S. Pat. No. 5,200,248 to Thompson, et al., and U.S. Pat. No. 5,972,505 to Phillips, et al., the entirety of each of which is incorporated herein by reference.

The channels of a fiber 20 can be designed so as to encourage flow there through via capillary action. For instance, a capillary channeled fiber 20 can have channel wall thicknesses of less than about 50 μm, less than about 10 μm, or less than about 5 μm, in one embodiment. The width of an individual channel can generally be less than about 0.5 mm, for instance less than about 0.3 mm, or less than about 0.1 mm. Channel widths from about 5 μm to about 0.5 mm can be used, for instance from about 30 μm to about 100 μm. The individual channels of a fiber 20 can generally be between about 15 μm and about 50 μm in depth, i.e., the height of the walls defining a channel there between. The capillary channels can be of any suitable shape. For instance a channel can define a regular cross-sectional shape (e.g., U-shaped, V-shaped, etc.), or can be irregular in cross-sectional shape. Generally, the capillary channels of a fiber can be of regular cross-sectional shape, with capillary channel walls that are substantially parallel to one another in cross-section. The capillary channel walls can be substantially perpendicular to the straight chords closing the capillary channels to which the wall serves as a boundary, though this is not required.

In one embodiment, a capillary channeled fiber 20 can satisfy the equation:

$$(1-X\cos(\theta_a)<0,$$

wherein $\theta_a$ is the advancing contact angle of water measured on a flat film of the same material make-up as the fiber, X is a shape factor of the fiber cross-section that ranges from about 1.2 to about 5 and satisfies the equation $$X = \frac{P_W}{4r + (\pi - 2)D}$$

wherein $P_w$ is the wetted perimeter of the fiber (i.e., the complete perimeter of the entire fiber cross section)

r is the radius of the fiber cross section (the radius of the circle circumscribing the entire fiber cross-section, and D is the minor axis dimension across the fiber cross section.

In another embodiment, a fiber can satisfy the equation $$(1-X\cos(\theta_a))<-0.7.$$

In general, the capillary channeled fibers can be polymeric, though this is not a requirement of the fibers. When considering polymeric capillary channeled fibers, a polymer forming the fiber can generally be of an amorphous or semicrystalline character. Particular polymers as may form a capillary channeled fiber 20 can include degradable or non-degradable biocompatible polymers, depending upon the desired application of the device. For instance, if the capillary channeled fibers are a component of an implantable tissue engineering scaffold, it may be desirable to utilize degradable biocompatible fibers.

Examples of suitable polymers include, but are not limited to, polyesters, polylactides, poly-®-hydroxybutyrates, polycaprolactones, polyglycolides, polyetheresters, rayon, acetate, polyamides (e.g., nylon), polyolefins, polyacrylates, polydioxanones, polytrimethylene carbonates, polyanhydrides, polycarbonates, polyoxyalkylene ether, polyurethanes, alkylene oxide compounds, polysaccharides, polyphosphazenes, polyethylene oxide-polypropylene glycol block copolymers, fibrin, polyvinyl pyrrolidines, hyaluronic acid, collagen, chitosan, polyvinyl alcohol, copolymers and blends of such polymers, and the like.

Capillary channeled fibers as may be incorporated in a device are available in the retail market and include fibers available from, but not limited to, COOLMAX® and ANTRON® fibers, which are manufactured by Invista of Waynesboro, Va.; HIGHLIGHTS™ fibers, which are manufactured by Superior Threads of St, George, Utah; and 4DG™ fibers, available from Fiber Innovation Technology of Johnson City, Tenn., Different fabrication approaches can be utilized to form channeled polymer fibers 20 of the devices. For instance, extrusion processes as are generally known in the art such as melt spinning, wet spinning, and dry spinning can be used. Melt spinning as well as other spinning methods involve the use of an extrusion die (sometimes referred to as a spinneret) which has an orifice design which roughly corresponds to the cross-sectional shape of the capillary channeled fiber immediately upon exit from the die. Melt spinning involves melting the polymer (or a polymeric composition), applying pressure to extrude the melt through an extrusion die, and cooling and drawing the extruded structure to the desired size. Depending upon orifice design, processing conditions, polymer composition, and other factors known to those skilled in the art, the final cross-sectional shape of a fiber can deviate from the orifice design somewhat. The extrusion die orifice design, the polymer composition, the temperature at which it is molten, and processing conditions of the extruded composition during drawing and cooling can be of importance in forming a capillary channeled fiber 20.

A method can include forming polymeric capillary channeled fibers from amorphous or semicrystalline polymers that can resist breakage upon drawing over a relatively large temperature range, particularly as temperature approaches the glass transition temperature. Whereas such polymers are commonly extruded at relatively high temperatures, a formation method can include operating the extruder at temperatures closer to the glass transition point to reduce viscosity of the melt and consequently facilitate higher polymer throughput through the extrusion die and obtain improved shape retention of the capillary channel structures relative to the extrusion die orifice design. However, as is known in the art, the optimal temperatures for extrusion will vary from polymer to polymer. Following extrusion, the nascent fiber can be cooled relatively rapidly during a drawing process for shape retention.

In one embodiment, two or more capillary channeled fibers 20 can be combined together to form a bundle, as is illustrated in FIG. 1. As can be seen, when bundled together, the bundle includes the channels of each fiber as well as one or more closed channels 21 formed between the two adjacent fibers. Closed channel 21 can function as a conduit to carry materials through a device in a semi-isolated state. For instance, channel 21 can function as a closed channel, but can still maintain communication and interaction with the surroundings due to the junctions formed between the adjacent fibers. Thus, a channel 21 formed between adjacent fibers can provide both the fluid transport properties of a closed channel and the interaction with the surrounding environment of an open channel. These inter-fiber spaces can enhance the wicking rate. The multiple fibers can be bundled by any of various mechanism, e.g., twisted, braided, intertwined, knotted, patterned weave, etc. The specific pattern of bundling can be designed to vary the inter-fiber spaces as desired, which can be used to adjust the transport properties of the bundle of fibers.

Fluid conduits as provided by the bundles of capillary channeled fibers 20 can also include additives such as biologically active agents or other materials either within the polymeric structure of the fibers or attached to the surface of the fibers, such as coatings to affect fluid flow. For instance, capillary channeled fibers can include growth factors, antibiotic agents, and the like incorporated within the fiber structure that can leach out of the fiber for release or can be released as a fiber degrades.

Biologically active agents can be located on the surface of a fiber according to any suitable coating or surface application process. For instance, biologically active agents can be temporarily or permanently bonded to a capillary channeled fiber 20. In general, an agent can be bonded to a fiber via an existing chemical functionality of the agent, such as amine, carboxylate, or thiol groups that can allow covalent, non-covalent, charge/charge, or any other type of bonding of the agent to a fiber surface while maintaining the desired activity of the agent. In such an embodiment, the base fiber composition can be selected so as to incorporate an anchoring mechanism for the agent. By way of example, a biologically active agent that includes a protonated amine functionality can be bonded to a polymeric fiber surface including negative charge groups.

Surface chemistry modification of a fiber can also be carried out to form a coating or alter the surface characteristics of the fibers and/or to encourage bonding of a biologically active agent to the fiber. Fiber surface chemistry modification processes can include, without limitation, alkaline treatments, plasma treatments, and the like. Fiber surface modification can encourage bonding of an active agent to the surface via any means. For example, fiber surface modification can increase the number of carboxylate groups on a fiber surface available for bonding to a desired active agent.

According to one embodiment, a grafting process may be employed for functionalizing a fiber surface with a desired chemistry. For instance, an at least bifunctional polymer possessing desired reactive functional groups such as carboxy, anhydride, amino or hydroxy groups may be first grafted to a fiber surface utilizing a portion of the functional groups of the polymer. Remaining functional groups of the polymer may then be utilized to attach additional functional materials to the fiber surface, e.g., biomolecules, microparticles, nano-particles, and the like. For example, a poly(ethylene terephthalate) (PET) fiber can be modified to include a polyacrylic acid layer, with further functionalization as desired to incorporate specific biologically active agents at the fiber surface. Surface modification of substrates in accordance with this grafting process is taught by U.S. Pat. No. 7,026,014 to Luzinov, et al., the entirety of which is incorporated herein by reference.

Direct surface modifications can also be used to establish a surface to which active ingredients can be anchored. For example, a polyamide fiber surface can be treated with ethylene-diamine to form a surface that is rich with both carboxylate and amine functionalities that can then be utilized to bond specific biologically active agents.

A plurality of fibers can be combined to form a bundle according to any desired method. For instance, a bundle of fibers can include 2 or more fibers, for instance from about 2 to about 10 fibers, or from about 3 to about 7 fibers can be combined to form a bundle. Fibers can be combined through simply mechanical means, for instance by twisting, braiding, knotting, intertwining, weaving, etc. a plurality of fibers together, or the fibers can be adhered together, for instance under pressure and heat or by use of an adhesive to form spot bonds between the fibers, provided, however, that any bonding process does not deform the capillary channels of the fibers and prevent or interfere with flow through the channels.

Figure 2A:
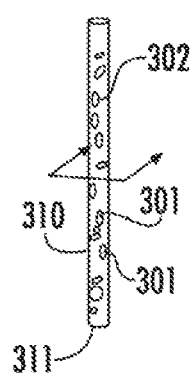
FIG. 2A illustrates a complete fiber bundle following separation of cells and FIG. 2B illustrates the fiber bundle separated into a top region and a bottom region.
Figure 2B:
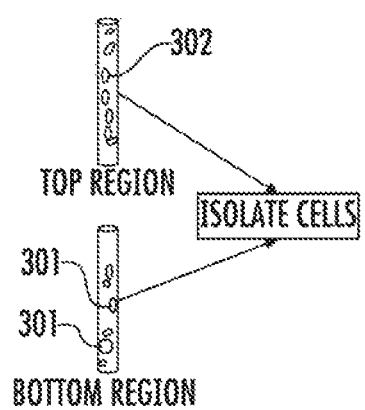

The materials transport devices can be diagnostic devices that utilize the capability of the capillary channels of the fibers to differentially transport cells in a test sample. FIG. 2 schematically illustrates a bundle 310 of capillary channeled fibers as may be incorporated in a device and includes FIG. 2A, which illustrates a complete fiber bundle and FIG. 2B, which illustrates the fiber bundle split into a top region and a bottom region. During use, the bundle 310 can be located in a vertical orientation in a test sample that includes a first cell type 301 and a second cell type 302 with a first end 311 of the bundle 310 in the test sample. The transport properties of the device can cause the cells 301, 302 to be wicked up the channels of the bundle 310. Following a period of time for wicking, generally about 15 minutes or more, for instance between about 15 minutes and 1 hour for a fiber or fiber bundle of a height of about 5 cm (for instance between about 2 and about 10 cm), the cells within the sample will preferentially rise to a height within the bundle 310 depending upon the cell type. For instance, as shown, the cells 301 can preferentially remain in the bottom region of the bundle 310 and the cells 302 can preferentially rise to the top region of the bundle 310. It should be understood that a device can be utilized to separate multiple cell types, and is not limited to separating only two cell types from one another, Without wishing to be bound to any particular theory, it is believed that the mechanism for cell separation within the channels of the fibers or fiber bundles is due to the physical and functional properties of the cells, wicking characteristics of the fibers, and the cell-fiber interaction. Physical properties that may play a role include cell size, deformability, surface friction or charge, and expression of cell adhesion molecules. For instance, the size and shape of the cells may play a role in the ability for cells to penetrate smaller channels created from the bundling of the fibers, Fiber bundle architecture can affect the wicking rate and vertical displacement of different cell types. For example, cross-sectional images of wicking fiber bundles depict channel and inter-fiber spaces sizes ranging from 5 µm to 95 µm. The size of the individual fibers, the tension of a bundle, the hydrophobicity, and the inter-fiber space can all play a role in the wicking of liquid and cell-interaction.

Other cellular properties that are believed to influence vertical movement of cells within a channel include cell membrane impedance, expression of adhesion molecules, and cells stiffness. As is known, membrane impedance, cell dielectric properties and cell electric properties vary between cell types. Electrical properties of the cell can influence the cell-interaction with the fiber and the resultant vertical movement. Cells with greater impedance or surface charge may have more interactions with a fiber, hindering the vertical cell movement. By way of example, it has been found differences in cellular impedance of cancer cells of varying aggressiveness. Specifically, it has been found that a more aggressive cancer cell type can have a significant reduction in impedance as compared to a less aggressive cancer cell. Additionally a correlation has been found between metastatic progression and membrane impedance reduction. Cell-fiber interaction and overall cell displacement of cell types can thus be affected by different membrane impedance of the different cell types.

Expression of cell adhesion molecules can also play a role in the cell-fiber interaction and ability of a cell to move through a confined space. Metastatic cells have been shown to lose endothelial adhesion molecules and transition into a more motile mesenchymal phenotype. For instance, cancerous cells with fewer adhesion molecules may have less surface friction and altered shape and can thus have less interaction with the fiber allowing the cells to wick greater distances.

Cell deformability can influence the ability of cells to deform, penetrate, and wick vertically through the channels of a fiber or fiber bundle. In general, research has shown that cancer cells have a significantly lower young's modulus compared to normal cells. Researchers have found a correlation between increased metastatic potential of cancer cells and higher deformability. Thus, cancer cells may be much softer and deform easier, allowing them to migrate more readily.

Knowledge with regard to differences between cell types to be separated (e.g., difference in stiffness, morphology, size, membrane impedance, etc.) can be used to design a device for optimal separation of cell types. For instance, given a known difference in size between cell types, the fibers of the device can be formed with particular channel sizes so as to better exclude or slow the passage of the larger cell type. Similarly, the stiffness or shape of the fibers and/or channels can be designed to optimize separation of particular cell types having known differences in characters. In one embodiment, the fibers can be surface functionalized to interact more strongly with one cell type than another based on differences in adhesion molecules or other cell surface receptors on the different cells. In addition, the hydrophobicity of the fibers can be varied, which can alter cell interaction and wicking behavior of the cells along the fiber channels.

Figure 3:
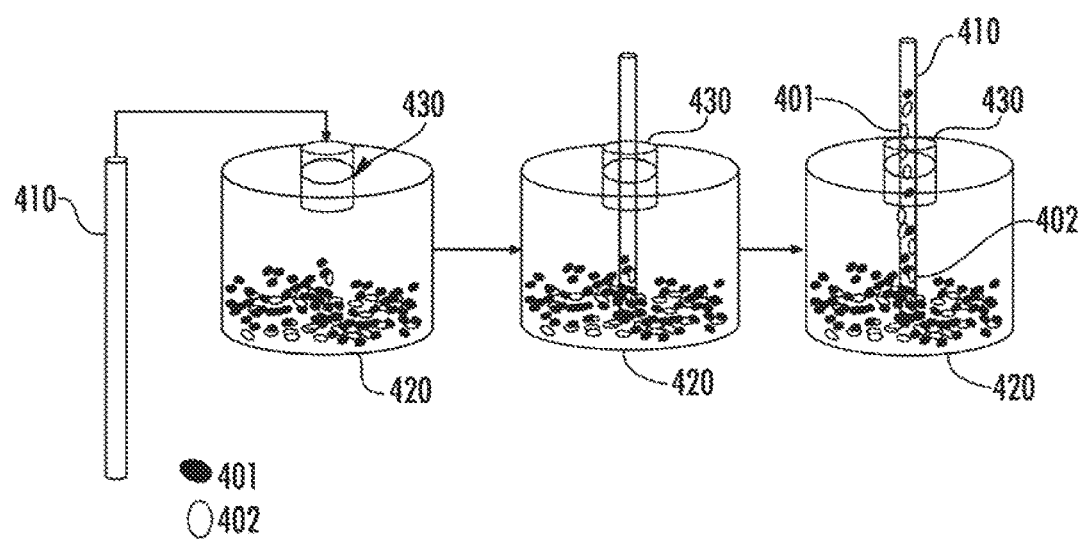
FIG. 3 is a schematic illustration of a diagnostic device employing the materials transport device.

FIG. 3 illustrates one embodiment of a materials transport device that incorporates a capillary channeled fiber or fiber bundle. As can be seen, the device of FIG. 3 is a vertical test system that can be used to analyze the vertical movement of a mixture of different cells 401, 402 along the fiber or fiber bundle 410.

The device includes a well 420 and a brace 430 for holding the fiber or fiber bundle 410 in a vertical orientation within the well. The brace 430 can be any structure that can hold the fiber or fiber bundle 410 in a vertical orientation with a first end of the fiber or fiber bundle 410 within the well 420. For instance, a brace 430 can include a supporting toroid of a size to hold the fiber or fiber bundle 410 securely in a vertical orientation. The brace 430 can be attached to the well 420 or free-standing, as desired. In another embodiment, the brace 430 can be a component of a lid for a well 420. For instance, a lid can include an aperture therethrough from the bottom side of the lid to the top side of the lid. The aperture can function as the brace 430 and can hold the fiber or fiber bundle 410 in a vertical orientation after the lid has been placed on the well 420.

During use, the fiber or fiber bundle 410 can be located with one end in the bottom of the well 420 such that the end is immersed in a mixture that includes the cell types 401, 402 to be separated. The fiber or fiber bundle 410 can be braced in a vertical orientation by use of the brace 430 and following a period of time the cells 401, 402 can differentially wick to different heights along the fiber or fiber bundle 410. Following the contact period, the cells can be removed from the fiber or fiber bundle 410 for further examination. For instance, the fiber or fiber bundle can be cut into separate regions (e.g., a top region and a bottom region) and the cells adhered to each region can be rinsed from the regions and further examined, as desired.

Figure 5:
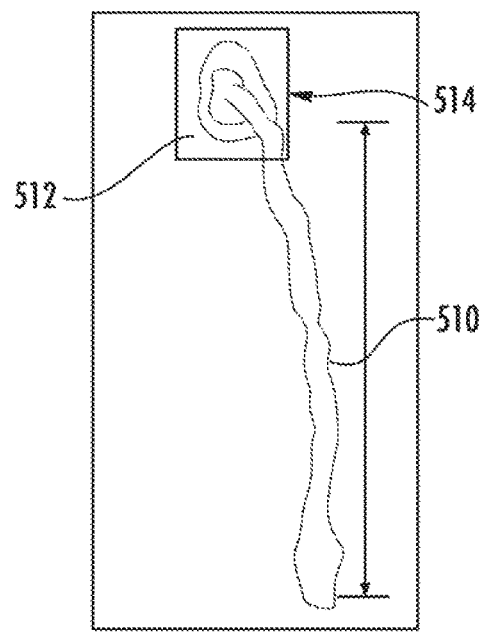
FIG. 5 illustrates one embodiment of a materials transport device as disclosed herein.
Figure 6:
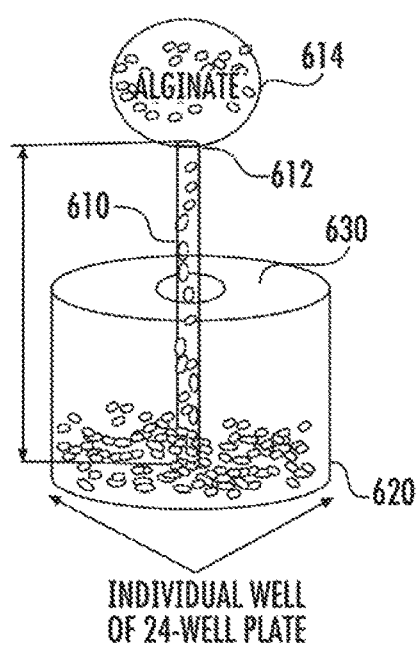
FIG. 6 illustrates the cell separation capability of a materials transport device as illustrated in FIG. 5.

In one embodiment the capillary channeled fibers can be combined with a sorptive material that can improve the wicking capability of the fibers. For instance, FIG. 5 and FIG. 6 illustrate bundles 510, 610 that include a plurality of capillary channeled fibers. At the end 512, 612 of each respective bundle 510, 610 is a cap 514, 614 that encloses one end of the bundle 510, 610. The cap includes a sorptive material that can encourage wicking through the fibers and further improve the transport capabilities of the device.

The sorptive material of the cap can include any sorptive hydrophilic material as is known in the art including both absorbent materials and adsorbent materials. The sorbent material can thus include any one of or combination of absorbent materials and/or elements and adsorbent materials and/or elements. Sorbent materials that may be used include fabrics, foams, fibrous structures and the like. Suitable materials include as non-limiting examples natural and synthetic polymeric absorbents, super-absorbents and celluloses. Fibrous absorbents manufactured from absorbent fibers such as alginate fibers and sodium carboxymethyl cellulose fibers, otherwise referred to as hydrofibers, are encompassed herein.

In general, absorbent materials are those that can sorb fluid through a process of absorption, similar to a sponge, in which a liquid diffuses into the volume and/or structure of the absorbent and becomes a part of that volume and/or structure. For example, the sorbent can pick up and retain a liquid distributed throughout its molecular structure causing the absorbent to swell. The liquid can cause the structure to swell about 50% or more, in one embodiment.

Certain exemplary embodiments of absorbents include, but are not limited to, comminuted wood pulp fluff, cellulose fibers, polymeric gelling agents, hydrophilic nonwovens, cellulose, sodium polyacrylate, cotton, polyethylene terephthalate, polyethylene, polypropylene, polyvinyl chloride, ABS, polyamide, polystyrene, polyvinyl alcohol, polycarbonate, ethylene methacrylate copolymer, polyacetal, etc., and combinations of adsorbent materials.

Adsorbents, on the other hand, remove fluid through a process of adsorption by retaining a liquid on their surface including pores and capillaries. Liquid accumulates on the surface of an adsorbent by forming a film of molecules or atoms that are retained thereon as a consequence of surface energy. In some embodiments, an adsorbent material can include one or more insoluble materials (or at least partially insoluble) that can be coated by a liquid on their surface. For example, the adsorbent can be a structure formed from insoluble fibers. The structure can be porous, as voids or spaces can be located between the individual fibers. Thus, liquid can accumulate on the surface of the fibers, thereby filling the voids between the fibers. Typical adsorbents will adsorb fluid without swelling more than about 50% in excess liquid.

Certain exemplary adsorbent materials include, but are not limited to, oxygen-containing compounds, carbon-based compounds, and/or polymer based compounds, among others. For example, adsorbent materials can include silica gels, alumina, zeolites, activated carbon, graphite, cellulose, porous polymer matrices, perlite, metal hydroxides, metal oxide filled cellulose acetate, butyrate and -nitrate, polyamide, polysulfone, vinyl polymers, polyesters, polyolefins and PTFE, polyurethane, as well as porous glass or glass ceramics, graphite oxide, polyelectrolyte complexes, etc., and combinations of adsorbent materials.

According to one embodiment, the sorptive material can be a hydrogel. Hydrogels are water-sorbable and generally cross-linked polymeric structures, usually having low modulus and compressive strength. Collagen is known to be an excellent hydrogel matrix material and has been found in diverse applications in regenerative medicine due to its biocompatibility and biodegradability. Alginate, a polysaccharide extracted from seaweed, has been used widely in tissue engineering applications due to its ability to gently gel in the presence of divalent ions such as calcium chloride.

According to another embodiment, a sorptive material can include an alginate sponge. Alginate sponges are highly porous, lyophilized substances with a lengthy history of use in connection with cell culture. The alginate of a sponge generally refers to pharmaceutical-grade plant-derived alginate. Pore size and shape is generally homogenous, with pores ranging from 50 to 200 µm in size. In one embodiment, the pores may be interconnecting. Alginate-based fibrous absorbents such as are used in dressings containing fibers of calcium alginate, or blends of sodium and calcium alginate, or fibers of sodium carboxymethyl cellulose can be utilized as a sorptive material.

The sorptive material can be further treated to provide additional functionality to the device. For instance, a sorptive material, such as a sorptive polymer can incorporate functional groups that can bind to cells and/or biomolecules to be transported by the device. In one embodiment the sorptive material can include growth factors or biomolecules to enhance cell development and/or to deliver biomolecules to an area in the scaffold.

The sorptive material can be altered by modifying the cross-linking, the amount enclosing the fibers, the type of sorptive material etc. Such modifications can change the displacement of cells and which cell types are collected, In one embodiment, the cap can be coated, for instance with a hydrophobic or water impermeable material that can isolate the interior of the cap and prevent Materials that collect in the cap from escape as well as to prevent sorption of materials in the local environment by the sorptive material of the cap. For example, the cap can be coated, for instance with a hydrophobic or liquid impermeable coating, to alter the degradation characteristics of the sorptive material and prevent fluid sorption from surrounding tissue. Coating materials can include, for example and without limitation, cyanoacrylates, agarose, polyethylene glycol, etc.

The cap including sorptive material can be attached to one end of a capillary channeled fiber or bundle of fibers according to any suitable means. For instance, the sorptive material can adhere to the end of a fiber or bundle through charge/charge interaction, through covalent or ionic bonding, by use of a biocompatible adhesive, and so forth.

The cap can cover one end of the fibers such that the fiber ends are enclosed within the cap. The cap can generally enclose a portion of the fiber or fiber bundle, for instance about less than about half of the fiber or fiber bundle, less than about one third of the fiber or fiber bundle, less than about 20%, less than about 10%, or less than about 5% of the fiber or bundle, in some embodiments.

Figure 4:
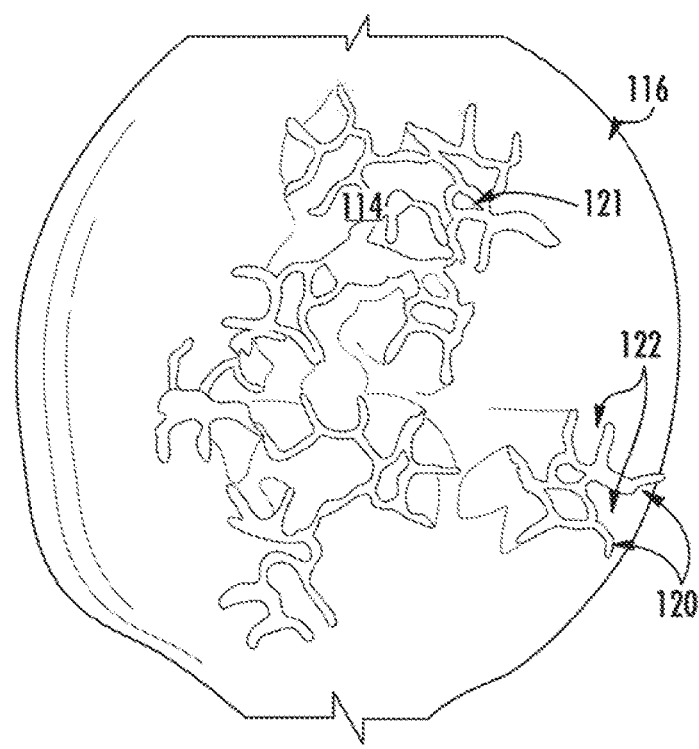
FIG. 4 illustrates a cross sectional view of bundled capillary channeled fibers.

FIG. 4 illustrates a cross sectional view of a sorptive cap 116 that encapsulates a bundle 114 of capillary channeled fibers 120. A cap 116 including the sorptive material can enclose the ends of the fibers 120 such that the channels 121 between fibers and the channels 122 along the fibers terminate within the cap 116. The sorptive qualities of the cap 116 can encourage wicking through the channels 121, 122 and improve materials transport through the fibers.

Diagnostic systems can be designed that incorporate the materials transport devices. As shown in FIG. 6, a diagnostic system including a well 620 and a brace 630 (in this embodiment a lid with an aperture therethrough) can utilize materials transport device that includes a fiber bundle 610 with a cap 614 enclosing one end 612 of the fiber bundle 610. The cap 614 can enclose the end of the fiber bundle 610 and encourage wicking through the channels of the capillary channeled fibers of the bundle 610.

The device includes a bundle 610 of cell- and liquid-wicking fibers of non-circular cross-section and a cap 614 that includes a biocompatible sorptive material, such as alginate. The cap 614 interfaces only one end of the bundle 610 as described earlier. The sorptive material and wicking fiber device can contact cells or tissue sample from a subject. Different cell types can be transported through the fibers and collect in the cap 614 at different rates. Thus, cells can be isolated and distinguished based on their vertical distance traveled in the fiber and collection in the cap 614. The device can be used as a diagnostic device by collecting or isolating cells in the cap 614 and/or the fiber bundle 610.

In one embodiment, the cap 614 can be removable. Thus, in this embodiment, following a period of wicking, the cap 614 can be removed and replaced with another cap that includes the same or different sorptive materials, and the second cap can collect different cell types moving at different rates, The materials transport devices can also be of benefit in tissue engineering applications. For example, a device that includes a bundle of capillary channeled fibers and a cap with a sorptive material can be incorporated in a tissue engineering scaffold matrix so as to improve transport of cells, nutrients, wastes, etc, throughout the scaffold. Accordingly, as a cellular construct develops on the scaffold, inclusion of one or more materials transport devices can not only encourage initial development of a large cellular construct, but can also prevent necrosis of new cells within the center of the developing tissue construct.

The device can transport fluids, biomolecules, and cells temporally and/or spatially to targeted locations within a tissue engineering scaffold. This device can be incorporated into a scaffold in various orientations to direct the movement of cell and biomolecules throughout the scaffold. For example, in one embodiment, the cap of the device can be located within the interior of the scaffold matrix and the second end of the bundle can be located outside of the scaffold matrix, for instance to target specific vascular or progenitor cell sources in the implant site. In this embodiment, the cap of the device can function as a passive pump and can encourage the flow of cells, nutrients, and biomolecules from the exterior are (e.g., surrounding tissue of an implanted scaffold) to be directed to the interior of the scaffold.

In one embodiment, the device can be incorporated into a scaffold matrix with the sorptive material cap on the exterior of the matrix and the bulk of the fiber bundle on the interior of the scaffold matrix. In this embodiment, the materials transport device can encourage the flow of wastes and harmful byproducts from the center of the scaffold to the exterior of the matrix (e.g., the surrounding implant site). Accordingly, the capillary channeled fibers can provide channels for the wastes to travel and the cap can function as a passive pump and in one embodiment can collect waste products within the cap.

One or more material transport devices can be incorporated within tissue engineering scaffolding matrices as are generally known in the art. In one embodiment; the overall diameter of a scaffolding matrix can be relatively large; for instance greater than about 10 mm, or greater than about 15 mm. For example, an engineering scaffold including a porous matrix and one or more material transport devices can be incorporated therein can be between about 10 and about 30 mm in cross sectional diameter, or about 20 mm in diameter. As utilized herein, the cross sectional diameter of a scaffold refers to the diameter of a circle that encloses a cross section of the scaffold. Thus, the tissue engineering scaffolds are not limited to any particular shape or geometry.

Fiber bundles of different devices within a scaffold can run generally parallel to one another or can run at angles to one another. In one embodiment, the fiber bundles of multiple devices can run generally parallel to one another, which can increase the mechanical integrity of the scaffold and the cellular construct that is developed on the scaffold. In one embodiment, the fiber bundles can be oriented based upon sources of vascular/growth factor/cell supply at the implant site.

The matrix of a tissue engineering scaffold can generally be a porous matrix that can encourage the growth and development of tissue thereon. In one particular embodiment, the matrix can be a polymeric matrix. Polymers of the matrix can include any biocompatible polymer and, in one embodiment, can include implantable polymers. In general, the preferred material of the matrix can depend upon the intended use of the scaffold. For example, in those embodiments in which a tissue construct developed on/in the scaffold is intended for implantation, the matrix can be developed so as to anticipate the implantation environment.

In general, any synthetic or natural polymer approved for human clinical use can be utilized in forming the porous matrix. For instance, polymers utilized in medical and pharmaceutical applications such as surgical suture materials or in controlled release devices can be utilized. By way of example, a scaffold matrix can be formed of one or more polymers including, without limitation, polyesters, polyanhydrides; polyorthoesters; polyphosphazenes; polyhydroxy acids such as polylactide (PL), polylactic acid (PL), polyglycolide (PG), polyglycolic acid (PGA); and polycaprolactone (PCL); aliphatic polyesters; poly(amino acids); polyalkylene oxalates; polyamides, poly(iminocarbonates); polyoxaesters; polyamidoesters; polyarylates; polyhydroxyalkanoates; peptides and polysaccharides such as agarose; dextran; hyaluronic acid; chitin; heparin; collagen; elastin; keratin; albumin; polymers and copolymers of lactide; glycolic acid; carboxymethyl cellulose; polyacrylates; polymethacrylates; epoxides; silicones; polyols such as polypropylene glycol; polyvinyl alcohol and polyethylene glycol and their derivatives; alginates such as sodium alginate or crosslinked alginate gum; polycaprolactone; polyanhydride; pectin; gelatin; crosslinked proteins; and the like.

In one embodiment, a polyester such as a copolymer of polylactide can be utilized. For instance copolymers of polylactide and polycaprolactone (e.g., ∈-polycaprolactone), polyglycolic acid, trimethylene carbonate, or p-dioxanone can be utilized in forming a scaffold matrix. These copolymers are biocompatible and bioresorbable in that their degradation products are low molecular weight compounds such as lactide and glycolic acid that can enter into normal metabolic pathways. Furthermore, copolymers of polylactide can offer the advantage of a large spectrum of degradation rates from a few days to years by simply varying the copolymer ratio of lactide to glycolic acid.

Polymers of a matrix can include lactide polymers such as poly(L-lactide) (PLL), poly(DL-lactide) (PDL), and copolymers thereof including poly(lactide-co-caprolactone) (PL/PCL). The co-monomer (lactide:caprolactone) ratios of a PL/PCL copolymer can generally be between about 100:0 and about 50:50. For example, the co-monomer ratios can be between about 85:15 and about 50:50. Blends of PL with PCL can also be utilized, for instance a PLL:PCL blend at a ratio between about 85:15 and 50:50 can be utilized.

A matrix can be formed of a biocompatible hydrogel and in one embodiment, an implantable hydrogel. For instance, a matrix can be formed of a biodegradable hydrogel. Suitable polymers of a matrix can include non-crosslinked and crosslinked polymers. A matrix including a crosslinked polymer can optionally include hydrolyzable portions, such that the portion can be degradable following implant of a tissue construct. For example, a hydrogel matrix can include a hydrolyzable component, such as polylactide. The crosslink density can be designed according to standard methods as are generally known in the art to control the rate of degradation of the matrix following implant, A matrix can be formed according to any method as is generally known in the art. For instance, a matrix can self-assemble upon mere contact of the various components or upon contact in conjunction with the presence of particular external conditions (such as temperature or pH). Alternatively, assembly can be induced according to any known method following mixing of the components. For example, step-wise or chain polymerization of multifunctional monomers or macromers can be induced via photopolymerization, temperature dependent polymerization, and/or chemically activated polymerization. Optionally, a matrix can be polymerized in the presence of an initiator. For example, in one embodiment, a matrix can be photopolymerized in the presence of a suitable initiator such as Irgacure® or Darocur® photoinitiators available from Ciba Specialty Chemicals. In another embodiment, a cationic initiator can be present. For example, a polyvalent elemental cation such as $Ca^{2+}$, $Mg^{2+}$, $Al^{3+}$, $La^{3+}$, or $Mn^{2+}$ can be used. In another embodiment, a polycationic polypeptide such as polylysine or polyarginine can be utilized as an initiator.

A scaffold matrix can include one or more additives. For example, in one embodiment, a tissue engineering scaffold can be utilized for the development of an osteogenic tissue construct, and ceramic additives can be included in the matrix. Polymer/ceramic composites can provide the structural stability and controlled degradation rate of implantable polymers in conjunction with improved osteogenesis through inclusion of a calcium phosphate mineral phase in the portion. For instance, polymer/ceramic composites as disclosed by Laurencin, et al. (U.S. Pat. No. 5,626,861), Laurencin, et al, (U.S. Pat. No. 5,866,155),and Armstrong, et al. (U.S. Pat. No. 6,417,247), all of which are incorporated herein by reference, can be utilized in a tissue engineering scaffold.

Bioactive agents as may be incorporated in a tissue engineering scaffold, either as a component of the matrix, as a component of a materials transport device (e.g., the capillary channeled fibers), or both can include growth factors (e.g., Transforming Growth Factor-beta (TGF-®)), nutrients and the like to encourage growth and development of a tissue construct on the scaffold. For example, the tissue engineering scaffold can include hormones, analgesics, anti-inflammatory agents, chemotherapeutic agents, anti-rejection agents, proteins and peptides (e.g., RGD peptides), polysaccharides, nucleic acids, lipids, and non-protein organic and inorganic compounds. Additives can include those that can exhibit biological effects such as osteogenic additives, osteoinductive additives, osteoconductive additives, growth factors, differentiation factors, steroid hormones, cytokines, lymphokines, antibiotics, and angiogenesis promoting or inhibiting factors and so forth.

To promote cell attachment, cell adhesion factors such as laminin, pronectin, or fibronectin or fragments thereof, e.g. arginine-glycine-aspartate, may be coated on or otherwise incorporated on or in a scaffold. A scaffold and/or the transport device may also be coated or have incorporated therein cytokines or other releasable cell stimulating factors such as; basic fibroblast growth factor (bFGF), transforming growth factor beta (TGF-®), nerve growth factor (NGF), growth factor-1 (IGF-1), growth hormone (GH), multiplication stimulating activity (MSA), cartilage derived factor (CDF), bone morphogenic proteins (BMPs) or other osteogenic factors, anti-angiogenesis factors (angiostatin), vascular endothelial growth factor, platelet-derived growth factor and insulin-derived growth factors (IGF).

DNA such as a gene sequence or portion thereof, coding for a growth factor or other of the auxiliary factors mentioned above may also be incorporated into a scaffold. The DNA sequence may be "naked" or present in a vector or otherwise encapsulated or protected. The DNA sequence may also represent an antisense sequence of a gene or portion thereof.

Additives can also include tracking or monitoring agents such as, without limitation, radiopaque materials such as barium, or other imaging agents.

It should be understood that any additive is not limited to any specific portion of the scaffolds. Additives may be incorporated in any suitable portion of a scaffold, as is known to one of ordinary skill in the art including one or more capillary channeled fibers, one or more fiber bundles, and/or any portion of a matrix.

The porosity of a matrix can be formed according to any methodology. In general, the porous matrix can define a porosity of between about 10 and about 90 volume %, for instance between about 20 and about 50 volume %, and a pore size of between about 30 µm and about 300 µm, for instance between about 50 µm and about 250 µm, or between about 100 µm and about 200 µm.

Figure 7:
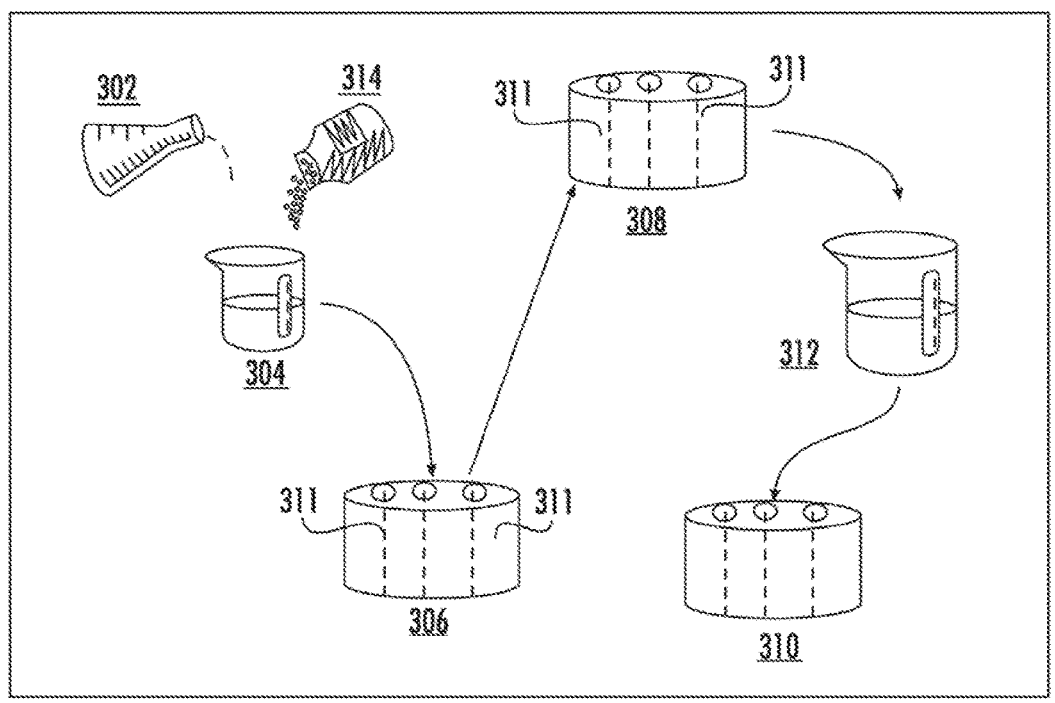
FIG. 7 is a schematic illustration of a production process as may be used to produce a tissue engineering scaffold as described herein.

According to one embodiment, the tissue engineering scaffold can be formed according to a particulate leaching method. FIG. 7 schematically illustrates one such method. As can be seen, a matrix can be formed by combining a mixture 302 including a polymer in a solvent with a sacrificial porogen 314 that will later be removed to provide the desired porosity. The composite mixture 304 thus formed is molded around a plurality of materials transport devices 311 held in a mold 306 and the solvent allowed to evaporate. Individual transport devices 311 can have a distance between one another to encourage transport of materials through the porous matrix. For instance, the individual transport devices 311 can be between about 1 mm and about 10 mm apart (e.g., center-to-center of the bundle spacing), or between about 3 and about 7 mm apart, in one embodiment.

The resulting mold 308 can then be heated slightly beyond the $T_g$ for the polymer of the matrix to ensure complete bonding of the polymer. Once cooled, the mold 308 can be placed in a solvent 312 such that the sacrificial porogen particles are dissolved or leached out to provide the tissue engineering scaffold 310. The porogen can be any suitable sacrificial material, such as a salt, a sacrificial polymeric microsphere, or the like.

Figure 8:
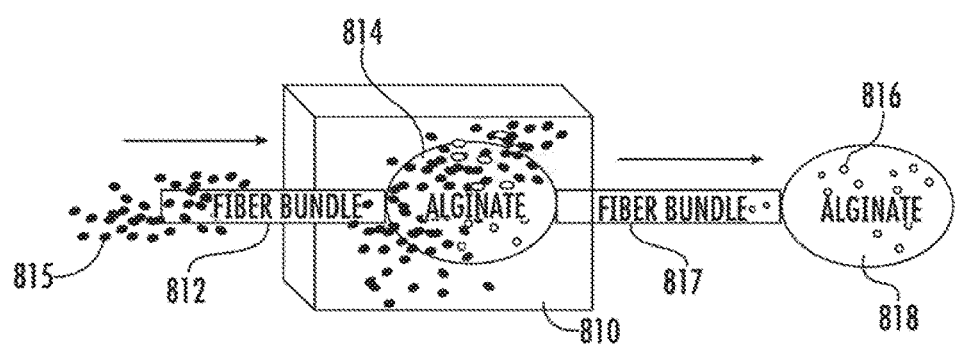
FIG. 8 is a schematic illustration of a tissue engineering scaffold incorporating a materials transport device as disclosed herein.

FIG. 8 illustrates another embodiment of a tissue engineering scaffold including a porous matrix 810, a first materials transport device that includes a first fiber bundle 812 and a first cap 814 on the first fiber bundle 812 and a second materials transport device that includes a second fiber bundle 817 and a second cap 818 on the second fiber bundle. In this particular embodiment, the two transport devices are attached to one another such that one end of the second fiber bundle 817 is enclosed within the cap 814 of the first device. This may prove helpful in encouraging transport of materials throughout the device, but is not a requirement of a scaffold. In other embodiments, multiple devices of a scaffold can be separated from one another, with a portion of the devices having the cap section within the scaffold and another portion of the devices having the cap section exterior to the scaffold. In another embodiment, the bundle of fibers can be directed toward the source or sources of the implant site and the absorbent material can be located within in the scaffold.

During use materials 815 including in one embodiment living cells can be transported into the scaffold in order to form a tissue engineered construct on/within the scaffold. Such cells include autograft cells which are derived from a patient's tissue and have (optionally) been expanded in number by culturing ex vivo for a period of time before being introduced onto a scaffold. Cell types can include cell types from any species. By way of example, human cell types as may be loaded onto a scaffold can include, without limitation, stem cells, diseased cells, myocytes, myoblasts, osteocytes, osteoblasts, epithelial cells, and combinations of multiple cell types.

Cells can be loaded onto a scaffold at any time during use, with the preferred loading timing/methodology generally depending upon the end use of the scaffold/construct. For instance, when considering an in vitro utilization, in which the tissue engineering scaffold may be utilized for study and/or development, but not necessarily for implant, the cells can be loaded following formation of the tissue engineering scaffold or even in conjunction with formation of the scaffold, for instance in conjunction with the formation of the matrix that surrounds one or more materials transport devices. When considering utilization of a scaffold in an implant application, cells can be loaded on the scaffold prior to implant, for instance at a time prior to implant such that a period of growth and development of the cells on the scaffold is carried out prior to implant. In one embodiment, ex vivo cells of the subject can be utilized, and the cells can be loaded on the implant at any time prior to implant. For example, ex vivo cells can be loaded onto a tissue engineering scaffold several hours or days prior to the implant procedure, so as to provide a time period for the cells to grow and develop on the scaffold, or alternatively, cells may be loaded on to the scaffold immediately prior to implant, for instance in the operating room prior to implant of the scaffold. In yet another embodiment, a tissue engineering scaffold may be implanted in a living subject without cells loaded on to the scaffold, and the scaffold may serve as a site for natural cell loading, growth, and development for the subject's own system following implant.

The second materials transport device can efficiently transport waste materials 816 from the interior of the scaffold 810 to the exterior field. In one embodiment, the waste materials 816 can be collected within the cap 818, for instance for examination.

The present disclosure may be better understood with reference to the examples, set forth below.

Example 1

Normal mouse mammary epithelial cell line, NMuMG (ATCC), was stably transfected with Green Fluorescent Protein (NMuMG-GFP). Cancer mouse epithelial cell line (cells isolated from a mammary tumor that spontaneously arose in a MMTV-neu transgenic female mouse) was stably transfected with Red Fluorescent Protein (MMTV-neu-RFP). NMuMG-GFP cells were cultured in Dulbecco's Modified Eagle's Medium (DMEM, Invitrogen) supplemented with 10% fetal bovine serum (FBS, Gibco), and MEGM single quots (Lonza) while MMTV-neu-RFP cells were cultured in DMEM (Invitrogen) supplemented with 10% FBS (Gibco), 10,000 U penicillin, and 10 mg streptomycin/mL (Sigma-Aldrich). Cells were cultured in a T150 flask (Corning) and maintained in a humidified incubator at 37° C. and 5% $CO_2$. Once cells were confluent, NMuMG-GFP at passage 4 and MMTV-neu-RFP at passage 5 were detached using trypsin-EDTA solution (Sigma) and resuspended in growth media to prepare for the vertical test.

Poly-L-lactide (Natureworks) wicking fiber was extruded with non-circular cross-sectional dimensions of 0.72 mm×0.55 mm. Each wicking fiber was sliced into multiple individual single wicking fibers of 3.5 cm and 10 cm in length. The 10 cm wicking fibers were used to form the wicking fiber bundles. Three of these fibers were twisted using an apparatus at 11 rotations per centimeter twist. The bundle was sliced into 3.5 cm long sections. Single and bundled wicking fibers were cleaned by soaking in three changes of ethanol for 1 hour, and placed under ultraviolet light for 6 hours. Samples were then soaked in phosphate-buffered saline (PBS, Invitrogen) solution for 2 hours and air-dried overnight in a sterile hood.

The vertical wicking test of cells utilized a device as illustrated in FIG. 4. The lid contained fitted holes with columns to securely hold the 3.5 cm wicking fibers and wicking fiber bundles vertical. Both cancer and normal cell lines were seeded in each well of a low attachment 12-well plate at a density of one million cells per well along with 1 mL of growth media. Single wicking fibers or wicking fiber bundles were vertically inserted through the columns so only the bottom 3 mm of the fiber was contacting the cell solution. The set up was placed on a flattop shaker (VWR) at 100 rpm in a humidified incubator at 37° C. and 5% $CO_2$. The vertical displacement of the mouse cancer and normal mammary cells along the wicking were determined at time points of 0.5, 9, and 24 hours with the initial time point being fiber placement into the cell solution.

To assess the cell displacement of both cell types the fibers were transferred to a well of 6-well plate, rinsed twice with phosphate-buffered saline solution, and fixed for 15 min with 4% paraformaldehyde. After the cells on the wicking fiber constructs were fixed, the fibers were transferred to microscope slides and the vertical displacement was evaluated using fluorescent microscopy and imaging software. The entire length of the fiber was imaged using fluorescent microscopy using 25× total magnification. FITC was used to view the vertical movement of normal cells transfected with Green Fluorescent Protein, and TRITC is used to view the vertical movement of cancer cells transfected with Red Fluorescent Protein. Imaging software was used to determine the vertical displacement (μm) of the cells in each image taken along the fiber. Images were aligned to qualitatively show the total displacement of both normal and cancer cells with total vertical displacement quantified by the summation of each individual image.

Figure 9:
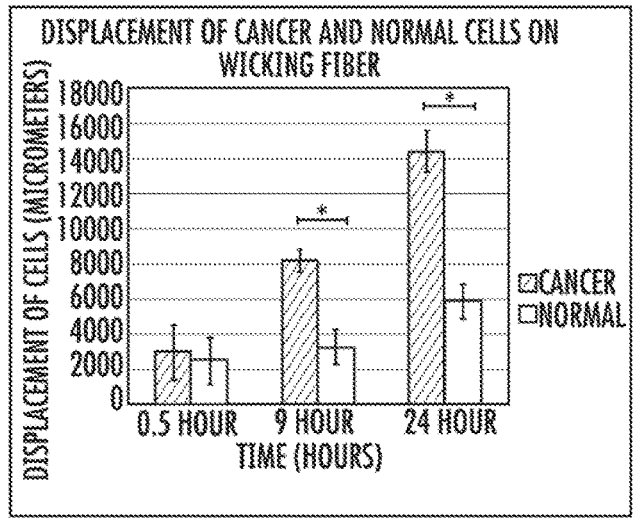
FIG. 9 illustrates the displacement of cancer and normal cells on a diagnostic device as described herein.

Images qualitatively showed a vertical separation of cancer cells and normal cells and depict higher cell densities of cancer cells along the fiber. Imaging software was used to quantify the vertical displacement (μm) of the cells in each image taken along the fiber. The total vertical displacement was found from the summation of each individual image along the fiber. Matched pairs test analysis was conducting using JMP statistical software to compare (p<0.05) the vertical displacement of MMTV-neu-RFP, cancer cells, and MMuMG-GFP, normal cells. The results showed the vertical displacement of MMTV-neu-RFP cells was significantly greater (p<0.05) than NMuMG-GFP cells after 9 hours and 24 hours (FIG. 9). Results suggest wicking fibers can separate cancer cells from a mixed cellular solution and potentially isolate the cancer cells from the top regions.

Example 2

Mammary epithelial cell line from benign breast tissue, MCF-10A (ATCC), was stably transfected with Green Fluorescent Protein (MCF-10A-GFP). Human breast cancer cell line, MCF-7, (ATCC) was stably transfected with Red Fluorescent Protein (MCF-7-RFP). MCF-10A-GFP cells, passage 5, were cultured in DMEM (Invitrogen) supplemented with 10% FBS (Gibco), 1% Fungizone, and MEGM single quots (Lonza). MCF-7-RFP cells, passage 6, were cultured in DMEM (Invitrogen) supplemented with 10% FBS, 1% Fungizone (Gibco), 10,000 U penicillin, and 10 mg streptomycin/mL (Sigma-Aldrich). Cells were cultured in a T-150 flask (Corning) and maintained in a humidified incubator at 37° C. and 5% $CO_2$. Once confluent both cell types were removed with trypsin-EDTA solution (Sigma-Aldrich) and resuspended in culture medium to prepare for vertical test.

Figure 10:
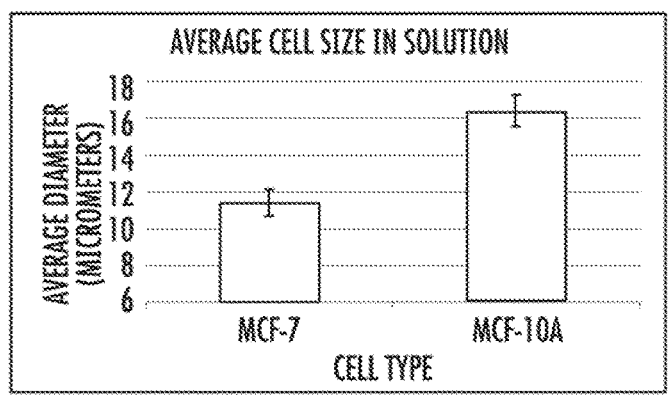
FIG. 10 graphically illustrates the difference in cell size between cancer and normal cells.

The average cell size of the MCF-7-RFP and MCF-10A-GFP cells was measured in cell solution. Cells were removed from culture flasks by adding trypsin EDTA solution. After incubation with solution for 15 min, 5 million cells were resuspended in 5 mL of growth medium in a 15 mL centrifuge tube. The centrifuge tube was vortexed to maintain the cells in solution. A volume of 10 μL of cell solution was added to five different microscope slides. The MCF-10A-GFP and MCF-7-RFP cells were imaged with the fluorescence microscope and measured with imaging software. The measurement function of the software was used to determine the average diameter of each cell line. Results are presented in FIG. 10.

A device and method as described in Example 1 was utilized to assess the cell displacement of both cell types. After 24-hours the vertical wicking fiber bundles were removed from the custom 12-well plate and the fibers were sectioned with a blade into a top and bottom region of the fiber. The top and bottom regions were placed in separate wells of a 24-well plate. The samples were rinsed with PBS twice and untwisted using forceps. The cells were removed by adding 500 μL of trypsin-EDTA solution into the well with the fiber region and placing the plate on a flat-top (VWR) shaker at 200 rpm in a 37° C. incubator. After 15 min the cells were resuspended in 500 μL of growth media and the number of MCF-10A and MCF-7 in both regions of the fiber were evaluated using guava easyCyte™ flow cytometry (Guava Technologies). The number of MCF-10A-GFP and MCF-7-RFP in each region was evaluated by following the manufacturer's instructions for InCyte software (Guava Technologies). Positive and negative controls with known cell densities were used to calibrate the machine before measurements on the treatments were taken.

The vertical displacement of the human cancerous and benign cells along the fiber bundles were determined at time points of 0.25 hours, 2 hours, 12 hours and 24 hours with the initial time point being fiber placement into the cell solution. The matched pairs test analysis in JMP was used to compare ($p<0.05$) the amount of MCF-7-RFP and MCF-10A-GFP in top and bottom regions of the fiber bundle. The results showed there were significantly more MCF-7-RFP cells in the top region of the fiber bundle than MCF-10A-GFP cells. There was no significant difference in cell count between cell types in the bottom region of the fiber.

Figure 11:
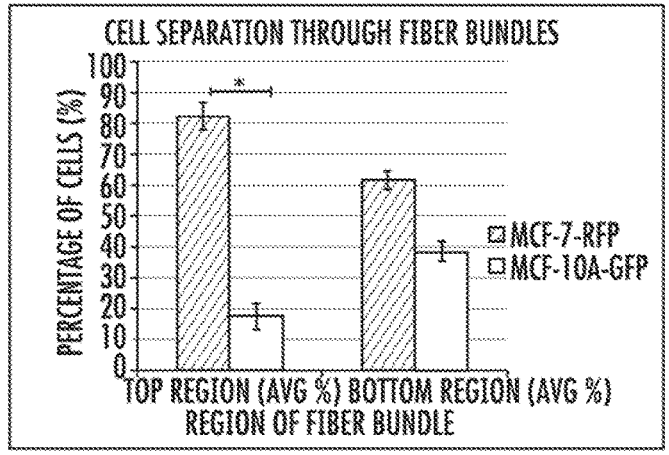
FIG. 11 illustrates the separation of cancerous and benign breast cells by use of a diagnostic device as described herein.

To quantify the separation the fibers were sectioned in half with a blade creating a top and bottom region. Each region was transferred to a new empty well, washed with phosphate-buffered saline, unwound with forceps, and soaked in Trypsin-EDTA solution to remove the cells. The cell count in each region of the fiber was determined using flow cytometry (Guava Technologies) with InCyte software (Guava Technologies). Both the complexity and size of the cells and fluorescent protein expression were used to quantify the number of cancerous and benign cells in each region. FIG. 11 illustrates the percentage of each cell type in top and bottom regions demonstrating a significant difference ($p<0.05$) between percentage of MCF-7-RFP and MCF-10A-GFP. These results make evident that the wicking fiber bundle can separate and isolate cancerous cells from a mixture with high purity, as the graph indicates 82% of cells isolated from top region are cancerous.

Example 3

To distinguish progenitor cells from a further differentiated cell line the following cell lines were used: D1 mouse mesenchymal stem cells (ATCC) and RAW mouse macrophage cells (ATCC). D1 and Raw cells were labeled with fluorescent probes, CellTracker Red CMTPX (Invitrogen) and CellTracker Green CMFDA (Invitrogen), respectively. A device and fiber bundles as described above in Example 1 were used. Both cell types were placed in each of the wells of a low attachment 12-well plate at a density of one million per mL. The fibers were vertically inserted into the custom-made lids designed to keep the fiber vertical and only 3 mm of the tip submersed. The displacement of the D1 and raw cells was determined at time points of 1 and 24 hours using fluorescent microscopy and imaging software. ImageJ was used to evaluate the cellular displacement and density of each cell type.

Figure 12:
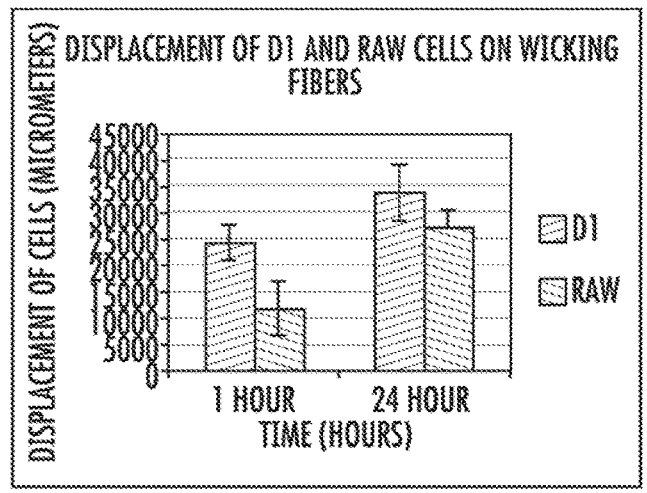
FIG. 12 illustrates the displacement of two different cell types on a diagnostic device as described herein.

Results are shown in FIG. 12. As can be seen, D1 cells exhibited greater vertical displacement and cell densities along the fiber than the RAW cells.

Example 4

Figure 13:
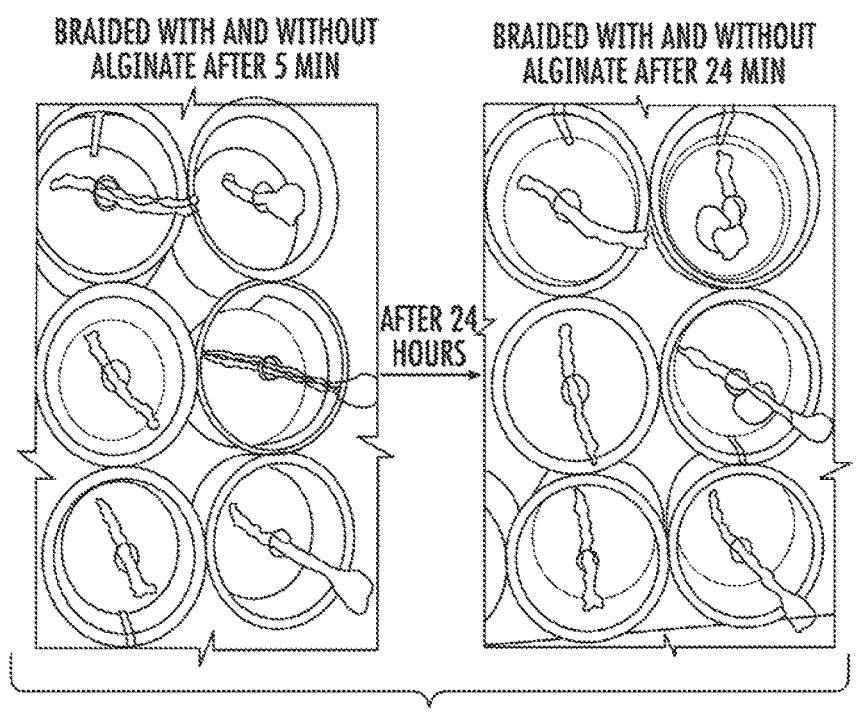
FIG. 13 illustrates diagnostic devices as described herein during use.

To evaluate the effect of an absorptive cap on the fluid transport of wicking fibers a vertical test with dye-solution was performed for samples containing only a bundle of three braided wicking fibers and samples containing a bundle of three braided wicking fibers with a globule of alginate on one end. The fluid transport of dye-solution in single wicking fibers and single wicking fibers with alginate is also evaluated. 1-mL of dye-solution was pipetted into each well of a 12-well plate. Three samples 4-cm in length containing only braided wicking fibers and three samples 4-cm in length with alginate were vertically placed into each of the wells. The end of the wicking fiber not containing the alginate was placed into the dye-solution of the well, as shown in FIG. 13. Three single fibers 4-cm in length and three single fibers containing alginate globules were also vertically placed in the dye-solution.

Figure 14:
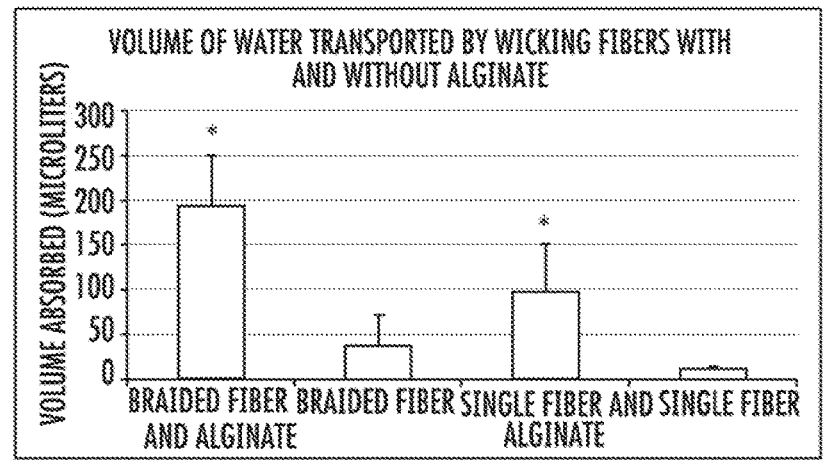
FIG. 14 compares the volume of water transported through various embodiments of a materials transport devices as described herein.

Each well of the 12-well plate initially contained 1-mL of dye-solution. After 24 hours of the vertical test the amount of volume left in the well was measured using a pipettor. The change in volume in the well before and after the vertical test was recorded as the volume absorbed as shown in FIG. 14. This chart quantitatively shows bundled fibers enhance the amount of liquid transported and absorbed compared to single fibers. The results also indicate that alginate increases the amount of liquid absorbed by the braided and single fibers. Students T-test shows a significant difference (*$p<0.05$) between each fiber set-up (i.e. braided or single) with and without alginate.

Example 5

A vertical test was conducted with a cell solution to evaluate the movement of cells through a device. The cell-solution contained two cell types, normal and cancer cells, of equal cell density of 500,000 cells/mL. The normal cell line and cancer cell line were labeled with green and red fluorescents, respectively, to analyze the vertical movement of different cell types. The test was performed for twelve samples containing a bundle of three braided wicking fibers and a globule of alginate on one end. 1 mL of cell-solution containing both cell types was pipetted into each well of a low-attachment 12-well plate. Four samples were imaged after the respected time points of 3 hours, 24 hours, and 48 hours taken from the experimental set-up.

Figure 15:
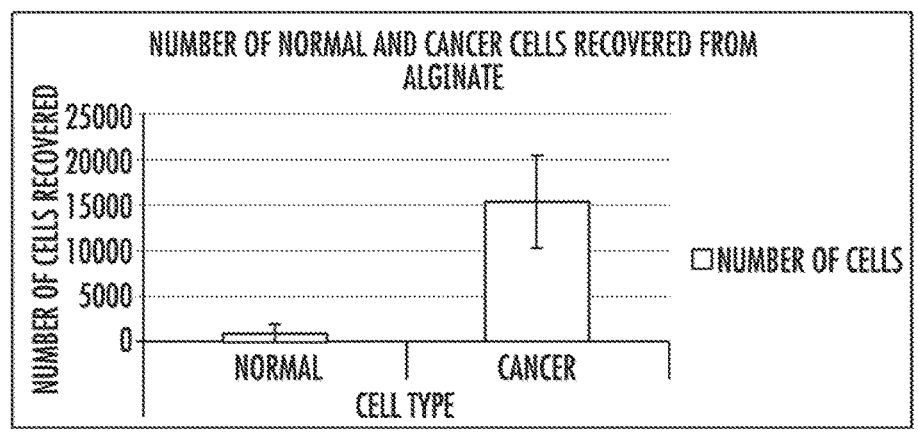
FIG. 15 illustrates the separation of normal and cancer cells by use of a diagnostic device as described herein.

After 24 hours the alginate was removed from each sample and dissolved allowing for the isolation of normal and cancer cells from the sample. A hemocytometer was used to count the amount of cancer and normal cells in the alginate components for each of the samples. FIG. 15 illustrates the results and shows the cancer cells collecting in the alginate more significantly than the normal cells ($p < 0.01$).

The results indicate the alginate wicking fiber construct can evaluate cell types and function as a diagnostic tool based on the vertical movement in the fibers and collection of cells in the alginate.

The amount of fibers and alginate used can increase the volume of fluid and cells transported. In another run, a bundle of 20 fibers and a volume of alginate five times the amount used previously were utilized. As a result, more fluid and cells traveled through the fibers and alginate in a shorter amount of time. The alginate collected approximately 10 times the amount of cancer cells as recorded in the previous run.

Example 6

Figure 16A:
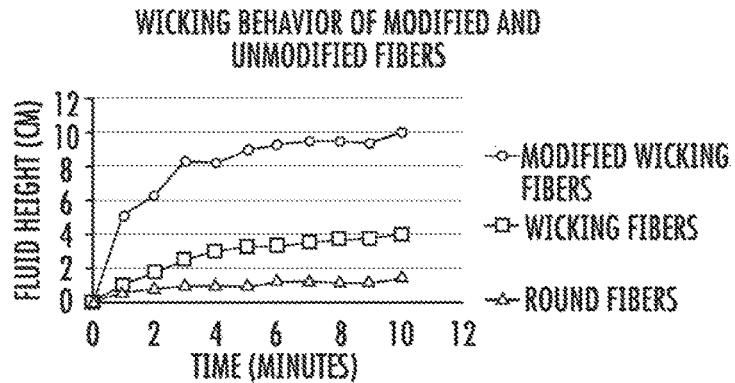
FIG. 16 presents the differences in transport capabilities for devices as disclosed herein incorporating channeled fibers as compared to round fibers. Results include the difference in wicking rate of constructs (FIG. 16A), the transport of cells to an upper region of devices (FIG. 16B) and the infiltration of cells into a scaffold incorporated with devices (FIG. 16C).

The transport properties of constructs including channeled polylactide fibers with an absorbent alginate cap, channeled polylactide fibers without the cap, and round polylactide fiber constructs were evaluated. The vertical wicking rates of these constructs were determined by analyzing the change in height of the liquid front over time. FIG. 16A illustrates the wicking rate of the capped constructs compared to the round and uncapped constructs. As can be seen, the capped channeled fiber constructs had enhanced fluid transport properties. The rate of the fluid front moving vertically was significantly greater in the capped construct than in round fiber or uncapped fiber constructs.

Figure 16B:
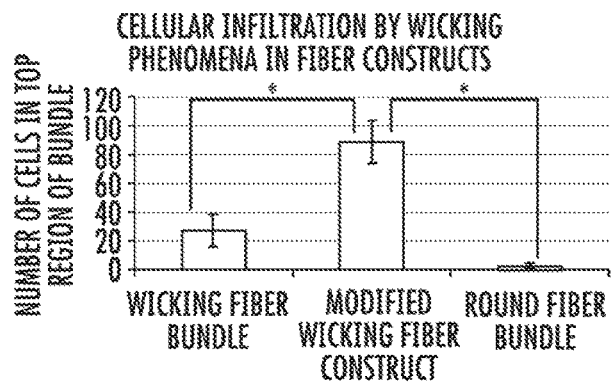

Bone progenitor cell penetration and retention was assessed in the capped fiber constructs and uncapped fiber constructs by assessing the vertical movement and cell densities of green-labeled D1 mouse mesenchymal progenitor cells (CellTracker green probe; Invitrogen) by fluorescent microscopy and quantifying cell movement along the constructs using Guava EasyCyte™ flow cytometry (Guava Technologies). Results are illustrated in FIG. 16B. As can be seen, there was significantly greater cellular recruitment into the top region of the capped constructs than into round or uncapped constructs. (Asterisks indicate significant differences ($p < 0.05$).)

Figure 16C:
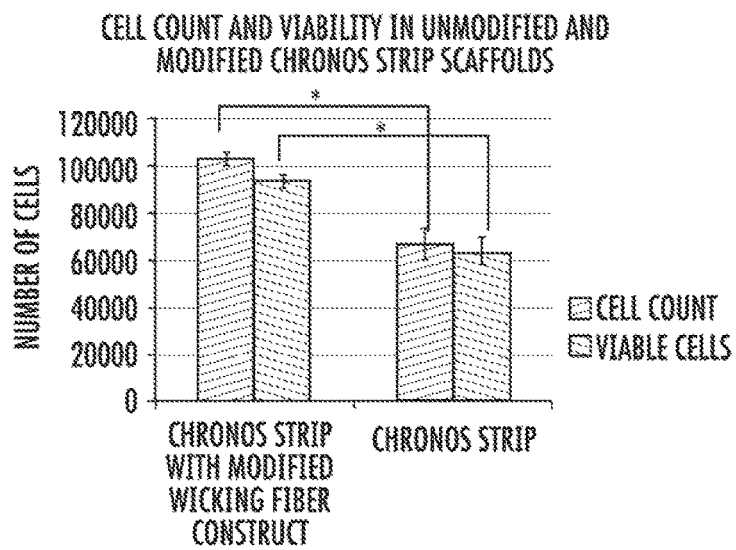

Capped channeled fiber constructs were also incorporated into chronOS® strip scaffolds and seeded using custom-made vacuum sealed perfusion packs. Samples were incubated at room temperature for 1 hour. Cell infiltration, distribution, viability, and proliferation into the scaffolds were assessed by (1) imaging fluorescent probes DAPI and phalloidin (Invitrogen) in the center and peripheral regions of the scaffold (2) Live/Dead cytotoxicity assay (Invitrogen) and Viacount assay using Guava flow cytometer, (3) PicoGreen Assay (Invitrogen) and biochemistry analyzer (YSI 2700). Results are shown in FIG. 16C. As can be seen, the scaffold-modified construct increased both overall cell count and number of viable cells as compared to the scaffold alone. (Asterisks indicate significant differences ($p < 0.05$).) The results also showed that the central interior region of the modified scaffold had enhanced cellular infiltration and distribution as well as significantly more viable cells and greater proliferation.

Example 7

Figure 17A:
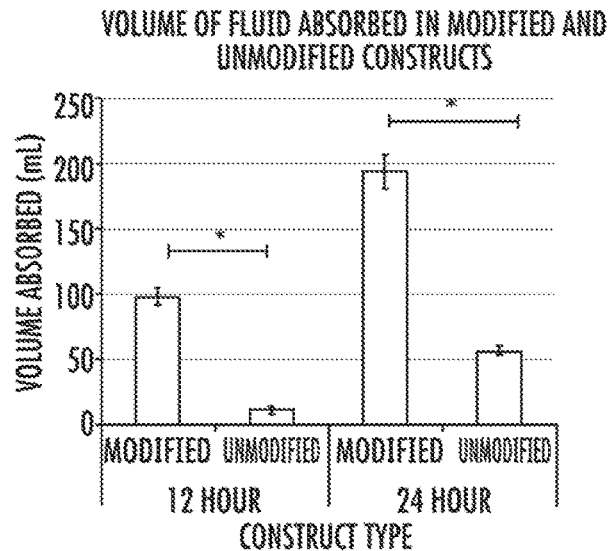
FIG. 17 presents the differences in transport capabilities for devices as disclosed herein including alginate absorbent caps on one end as compared to devices without the absorbent caps. Results include the difference in volume of absorbed fluid over time (FIG. 17A) and the percentage of cells isolated in the alginate-capped constructs (FIG. 17B).

The transport properties of a channeled fiber construct modified by inclusion of an absorbent alginate cap as described above and an unmodified channeled fiber construct were evaluated by comparing the rate of wicking and amount of fluid absorbed over time. The vertical wicking rate was determined by analyzing the change in height of the liquid front over time after placing the samples vertically in a well containing dye-solution. The volume of absorbed fluid was determined by measuring the amount of fluid remaining in the well. FIG. 17A demonstrates the volume of fluid absorbed in the modified and unmodified constructs. (Asterisks indicate significant differences ($p < 0.05$).) As can be seen, the modified construct showed enhanced fluid transport properties. The rate of the fluid front moving vertically was significantly greater in the alginate-capped samples. As shown, the amount of fluid absorbed after 12 hours and 24 hours was greater in the alginate-capped constructs as compared to the unmodified constructs.

The alginate-capped construct was used to separate and isolate cancerous mammary epithelial cells, MCF-7 (ATCC), from a mixture of benign mammary epithelial cells MCF-10A (ATCC) and MCF-7 cells. To track the separation of the cell lines, benign and cancerous cells were stably transfected with Green Fluorescent Protein (GFP) or Red Fluorescent Protein (RFP), respectively. The separation along the construct was evaluated at 3 hours, 24 hours, and 48 hours with fluorescent microscopy. After 24 hours the cells were removed from the constructs and the percentage of benign and cancerous cells were determined using Guava EasyCyte™ flow cytometry (Guava Technologies) by evaluating the percentage of red and green fluorescent count. Positive and negative controls of known cell densities were used to calibrate the machine before measuring the treatment groups.

Figure 17B:
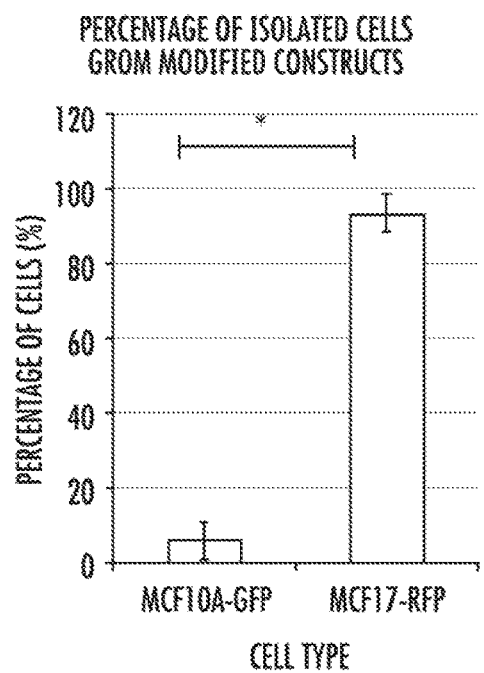

Fluorescent images of MCF7-RFP and MCF10A-GFP demonstrated separation of cancerous cells along the construct. FIG. 17B depicts a high percentage of cancerous MCF7-RFP cells isolated from the constructs after 24 hours. (Asterisks indicate significant differences ($p < 0.05$).)

Results indicate the alginate-capped construct showed enhanced transport properties that can be used for cell separation of normal and pathological cells. The results suggest the device can separate and isolate pathological cells from a mixture of cells in solution with high purity and efficiency. This device provides a rapid and label-free approach to isolate various cell types for pathological tissue test system applications.

It will be appreciated that the foregoing examples, given for purposes of illustration, are not to be construed as limiting the scope of this disclosure. Although only a few exemplary embodiments of the disclosed subject matter have been described in detail above, those skilled in the art will readily appreciate that many modifications are possible in the exemplary embodiments without materially departing from the novel teachings and advantages of this disclosure. Accordingly, all such modifications are intended to be included within the scope of this disclosure. Further, it is recognized that many embodiments may be conceived that do not achieve all of the advantages of some embodiments, yet the absence of a particular advantage shall not be construed to necessarily mean that such an embodiment is outside the scope of the present disclosure.

What is claimed is:

1. A diagnostic device comprising:
   a well that is configured for holding a fluid sample;
   a capillary channeled fiber having a longitudinal axis along a length of the fiber an outer surface, and a non-circular cross section that is perpendicular to the longitudinal axis of the fiber, the capillary channeled fiber including a plurality of co-linear channels extending along the entire length of the fiber, each channel being open at the outer surface of the fiber, each channel being defined by two opposed walls, each wall that extending in a first direction that is along the length and parallel to the longitudinal axis of the fiber and each wall also extending in a second direction that is perpendicular to the longitudinal axis of the fiber with each wall forming a side wall of one channel and each wall forming a part of the exterior surface of the fiber; and
   a brace located in or above the well, the brace comprising a structure that secures the capillary channeled fiber in a vertical orientation with a first end of the fiber within the well.

2. The diagnostic device of claim 1, wherein the brace is a lid configured to cover a top of the well, the lid including an aperture that passes from a first side of the lid to a second side of the lid, the aperture being configured to secure the fiber.

3. The diagnostic device of claim 1, wherein the capillary channeled fiber is a member of a bundle of fibers that are held adjacent to one another and generally aligned with one another in the bundle.

4. The diagnostic device of claim 3, wherein the fibers of the bundle are held adjacent to one another and generally aligned with one another such that at least one closed channel is formed between two adjacent capillary channeled fibers of the bundle.

5. The diagnostic device of claim 1, wherein the device further includes a cap that covers and is attached to a second end of the capillary channeled fiber with the second end of the capillary channeled fiber enclosed within the cap, the cap including a sorptive material that surrounds the second end of the capillary channeled fiber.

6. A method for separating biological materials by use of the device of claim 1, the method comprising:
   locating a fluid sample that includes a first biological material and a second biological material within the well, the first biological material wicking through the channels of the capillary channeled fiber to a first location of the device during a period of time and the second biological material wicking through the channels of the capillary channeled fiber to a second location of the device during the period of time; and
   recovering at least one of the first biological material or the second biological material sell from the device.

7. The method of claim 6, wherein the first biological material is a cancer cell and the second biological material is a healthy cell, the two cells being of the same cell type.

8. The method of claim 7, wherein the two cells are breast epithelial cells.

9. The method of claim 6, wherein the first biological material is a progenitor cell and the second biological material is a differentiated cell.

10. The method of claim 9, wherein the first biological material is a mesenchymal stem cell.

11. The method of claim 9, wherein the second biological material is a macrophage cell.

12. The diagnostic device of claim 5, wherein the sorptive material is an adsorptive material.

13. The diagnostic device of claim 5, wherein the sorptive material in an absorptive material.

14. The diagnostic device of claim 5, the cap comprising an alginate.

15. The diagnostic device of claim 5, the cap comprising a coating that includes a hydrophobic or water impermeable material.

16. The diagnostic device of claim 1, wherein the width of each of the co-linear channels is less than about 0.5 millimeters.

17. The diagnostic device of claim 1, wherein the capillary channeled fiber is a polymeric fiber.

18. The diagnostic device of claim 17, the polymeric fiber comprising a biocompatible polymer.

19. The diagnostic device of claim 1, the capillary channeled fiber comprising a biologically active agent within or on the surface of the fiber.

* * * * *